May 30, 1972 F. W. ANDERSON Plant Pat. 3,202
NECTARINE TREE
Filed Jan. 26, 1971
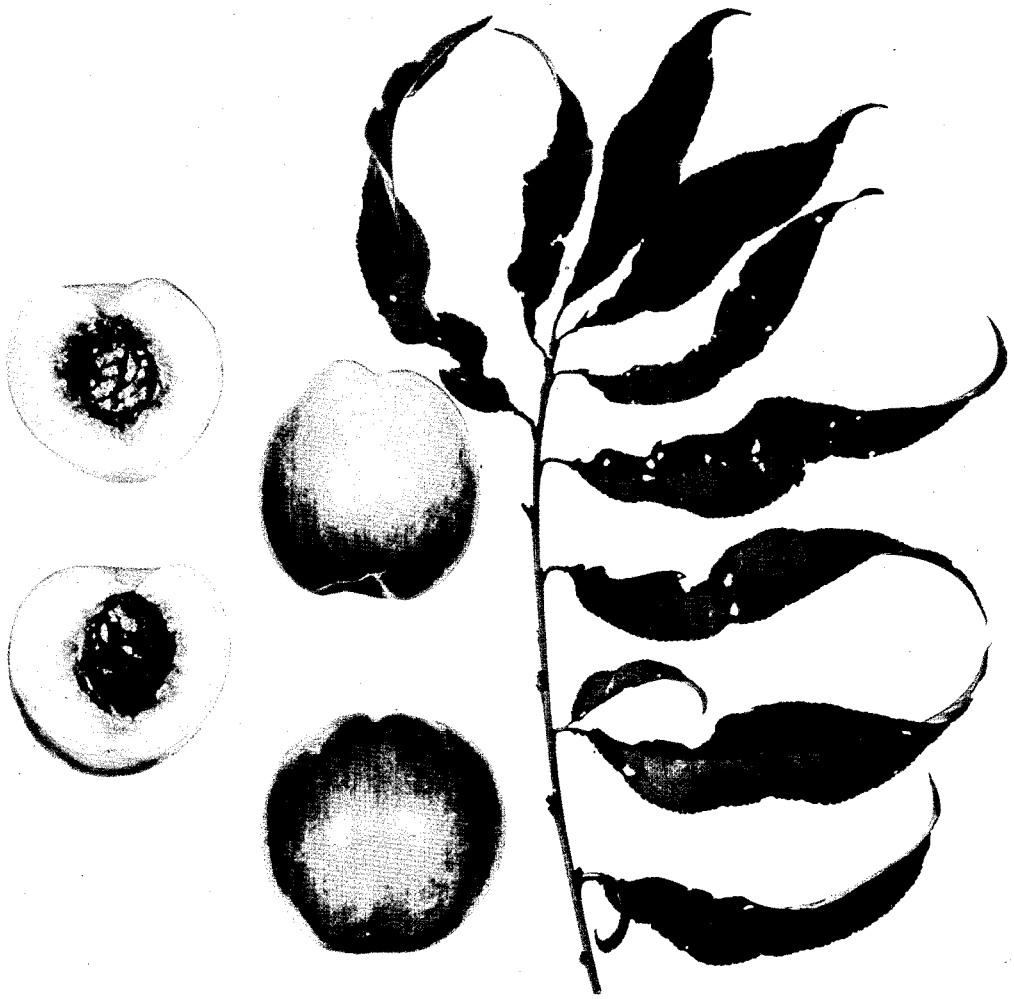
INVENTOR
Frederic W. Anderson
BY
Webster & Webster
ATTORNEYS United States Patent Office Plant Pat. 3,202
Patented May 30, 1972

3,202
NECTARINE TREE

Frederic W. Anderson, Merced, Calif., assignor to Reedley Nursery, Inc., Reedley, Calif.

Filed Jan. 28, 1971, Ser. No. 110,674
Int. Cl. A01h 5/03
U.S. Cl. Plt.—41 1 Claim

ABSTRACT OF THE DISCLOSURE

A nectarine tree of medium size, medium vigor, spreading, and a very productive bearer of uniform, freestone fruit of medium size and symmetrical globose form; the fruit, which is late in harvest, having yellow skin substantially overspread with red, and yellow flesh with red streaked thereinto from the pit cavity.

*Background of the variety*

Over a substantial number of years I have engaged in an extensive and continuing plant breeding program at my experimental nursery and orchard located near Le Grand, Merced County, Calif.; one purpose of such program being to provide improved varieties of fruit trees. The present variety of nectarine tree resulted from my endeavors in the conduct of such plant breeding program.

*Origin of the variety*

The present variety of nectarine tree was originated by me, in my experiment orchard located as aforesaid, as a second generation ($F_2$) seedling of a cross between the Sun Grand nectarine (United States Plant Patent No. 974) and an unnamed nectarine seedling. When the seedling of the present variety came into bearing, I recognized—upon continuing and careful observation—that it was new and distinct in important respects. I, therefore, undertook asexual reproduction of such variety in anticipation of subsequent introduction to the trade for commercial growing.

*Asexual reproduction of the variety*

I asexually reproduced the present variety of nectarine tree, in my aforementioned experimental orchard, by grafting on mature orchard trees, and, in maturity, such reproductions ran true to the original tree in all respects.

*Summary of the variety*

The herein claimed variety of nectarine tree is of medium size, medium vigor, spreading, and a very productive bearer of uniform, late-ripening, good quality, freestone fruit of medium size, symmetrical globose form, with yellow skin substantially overspread with red, and yellow flesh with red streaked thereinto from the pit cavity; the fruit being further characterized by some general resemblance to the Sun Grand but in harvest about two months later, and by greater resemblance to the Autumn Free (United States Plant Patent No. 2,976) but in harvest about one week later, with firmer flesh, higher sugar content, and a smoother skin which develops more red color over a larger portion of the fruit.

The late ripening of the freestone fruit, of the present variety of nectarine tree, is of considerable commercial importance in that the season, in the market, for fruit of such type is substantially extended.

*Brief description of the drawing*

The drawing is an illustration, by photographic reproduction in color, of a twig with leaves, and detached fruit, one of which is cut into halves to expose the flesh and with the stone remaining in place in one such half.

*Description of the variety*

The botanical details of this new and distinct variety of nectarine tree—with color definitions referenced in part to Maerz and Paul Dictionary of Color and otherwise in common color terms—are as follows:

Tree:
- *Size.*—Medium.
- *Vigor.*—Medium.
- *Growth.*—Spreading.
- *Productivity.*—Very productive.
- *Bearing.*—Regular bearer.

Trunk:
- *Size.*—Medium.
- *Texture.*—Medium.

Branches:
- *Size.*—Medium.
- *Texture.*—Smooth.

Leaves:
- *Size.*—Medium; average length—6¼"; average width—1¾".
- *Form.*—Lanceolate.
- *Thickness.*—Medium.
- *Texture.*—Smooth.
- *Margin.*—Crenate.
- *Color.*—Medium green.
- *Petiole.*—Medium length.
- *Glands.*—Number and position—usually 1 to 2 on petiole, and 2 to 4 on blade; alternate; medium size; reniform.

Flower buds:
- *Size.*—Medium.
- *Length.*—Medium.
- *Form.*—Plump.

Flowers:
- *Blooming period.*—About with the Sun Grand.
- *Size.*—Large; showy.

Fruit:
- *Maturity when described.*—Eating ripe.
- *Date of first picking.*—Sept. 15, 1970.
- *Date of last picking.*—Sept. 22, 1970.
- *Size.*—Uniform; Medium; average diameter axially—2⅜"; average transversely in suture plane—2⅜".
- *Form.*—Uniform; symmetrical; globose.
- *Suture.*—Distinct; Shallow; extends from base over entire circumference, with marked depression beyond pistil point.
- *Ventral surface.*—Rounded slightly.
- *Cavity.*—Elongated in suture plane with suture showing on one side.
- *Apex.*—Short; depressed.
- *Pistil point.*—Inconspicuous.

Skin:
- *Thickness.*—Medium.
- *Texture.*—Tough to medium.
- *Tendency to crack.*—Slight—none in dry season.
- *Color.*—Yellow (11–L–6) substantially overspread with red (5–L–5).

Flesh:
- *Texture.*—Firm; meaty; melting.
- *Fibers.*—Few; tender.
- *Ripens.*—Evenly.
- *Flavor.*—Delicate; sweet.
- *Aroma.*—Distinct.
- *Eating quality.*—Good.
- *Color.*—Yellow (10–K–5) with red (5–L–6) streaked into the flesh from the pit cavity. Flesh retains yellow color for several days after cutting and exposure to light and air.

Stone:

*Type.*—Free.

*Size.*—Medium; Average length—1¼"; average breadth—⅞"; average thickness—11/16.

*Form.*—Oblong.

*Base.*—Straight.

*Hilum.*—Broad.

*Apex.*—Rounded.

*Sides.*—Equal.

*Ridges.*—Rounded.

*Ventral edge.*—Thick.

*Dorsal edge.*—Full, with broad groove.

*Tendency to split.*—Slight.

*Color.*—Reddish brown.

Use: Market; dessert; local and long distance shipping.

Keeping quality: Good.

Resistance to insects and diseases: No unusual susceptibilities noted.

Shipping quality: Good.

The nectarine tree and its fruit herein described may vary in slight detail due to climatic and soil conditions under which the variety may be grown; the present description being of the variety as grown in the Central Valley of California.

I claim:

1. A new and distince variety of nectarine tree, substantially as illustrated and described, which is of medium size, medium vigor, spreading, and a very productive bearer of uniform, late-ripening, good quality, freestone fruit of medium size, symmetrical globose form, with yellow skin substantially overspread with red, and yellow flesh with red streaked thereinto from the pit cavity; the fruit being further characterized by some general resemblance to the Sun Grand but in harvest about two months later, and by greater resemblance to the Autumn Free but in harvest about one week later, with firmer flesh, high sugar content, and a smoother skin which developes more red color over a larger portion of the fruit.

No references cited.

ROBERT E. BAGWILL, Primary Examiner